US00PP18876P3

(12) United States Plant Patent
Spira et al.

(10) Patent No.: US PP18,876 P3
(45) Date of Patent: Jun. 3, 2008

(54) ASIAN PEAR TREE NAMED 'ASIO 6'

(50) Latin Name: *Pyrus pyrifolia*
Varietal Denomination: Asio 6

(75) Inventors: Joel S. Spira, Coopersburg, PA (US); Ruth R. Spira, Coopersburg, PA (US); Eugene S. Konno, Kempton, PA (US)

(73) Assignee: Subarashii Kudamono L.P., Coopersburg, PA (US)

( * ) Notice: Subject to any disclaimer, the term of this patent is extended or adjusted under 35 U.S.C. 154(b) by 107 days.

(21) Appl. No.: 11/434,208

(22) Filed: May 16, 2006

(65) Prior Publication Data

US 2007/0271639 P1 Nov. 22, 2007

(51) Int. Cl.
*A01H 5/00* (2006.01)

(52) U.S. Cl. ..... Plt./178

(58) Field of Classification Search ..... Plt./178
See application file for complete search history.

*Primary Examiner*—Annette H Para
(74) *Attorney, Agent, or Firm*—Buchanan Ingersoll & Rooney PC

(57) ABSTRACT

A new and distinct cultivar of Asian Pear tree is provided. The new cultivar forms attractive excellent quality late-season large conical to round fruit having a mottled reddish-brown russet surface with prominent tan lenticels and a very sweet mild flavor. The tree is medium-sized and possesses a well-branched upright growth habit. The leaves are medium green in coloration and possess pinnate venation and an acuminate apex. The fruit of the new cultivar has been found to be capable of storage for a longer period of time than most Asian Pear cultivars.

6 Drawing Sheets

Botanical/commercial classification: *Pyrus pyrifolia*/ Asian Pear.
Varietal denomination: cv. 'Asio 6'.

SUMMARY OF THE INVENTION

The present invention is a new and distinct Asian Pear cultivar.

The new cultivar was discovered as a distinctive seedling that germinated in 1983 in a test orchard at 1506 Pleasant View Road, Coopersburg, Pa., U.S.A. The new cultivar was discovered among thousands of seedlings that were produced for test purposes. The seed that produced the new cultivar of the present cultivar was obtained from Japan and was formed on open-pollinated Asian Pear trees. It is impossible to further identify the parent plants of the new cultivar. A single tree of the new cultivar was discovered following selective study and initially was designated No. 1175.

The original tree of the new cultivar first fruited in 1989 and has thereafter annually produced a crop of high quality Asian Pears.

It was found that the new cultivar of the present invention:

(a) forms attractive late-season large conical to round fruit having a mottled reddish-brown russet surface with prominent tan lenticels and a very sweet mild flavor, (b) forms a medium-sized tree having a well-branched upright growth habit, and (c) forms generally ovate medium green leaves with pinnate venation and an acuminate apex.

When compared to the 'Olympic' cultivar (non-patented in the United States), the new cultivar tends to bear slightly smaller fruit having a more conical shape. The surface fruit coloration is more mottled than the more uniform coloration of the 'Olympic' cultivar and the fruit of the new cultivar is optimally harvested when the surface coloration has a red hue. In contrast it has been found that the fruit of 'Olympic' cultivar is over mature when it begins to turn red. The fruit flesh of the new cultivar is more coarse in texture than that of the 'Olympic' cultivar and is comparable in crispness and juiciness. Also, the fruit of the new cultivar has been found to be capable of storage for a longer time than most other Asian Pear cultivars. For instance, the fruit of the new cultivar has been found to store well at 32° F. for up to approximately five months without breakdown and only slight skin shriveling. The new cultivar has been found to be susceptible to pear scab and fireblight.

Asexual reproduction of the new cultivar by budding on 'Bartlett', 'OHxF 97' and *Pyrus betulafolia* rootstocks (each non-patented in the United States) carried out at Aspers, Pa., U.S.A., beginning in 1990, and at Geneva, N.Y., U.S.A., beginning in 1997, has demonstrated that the characteristics of the new cultivar as described herein are firmly fixed and are retained through successive generations of such asexual propagation.

The new cultivar has been named 'Asio 6'.

BRIEF DESCRIPTION OF THE PHOTOGRAPHS

The accompanying photographs show in color as nearly true as it is reasonably possible to make the same in color illustrations of the character trees of the new cultivar and plant parts thereof.

Figure 1:
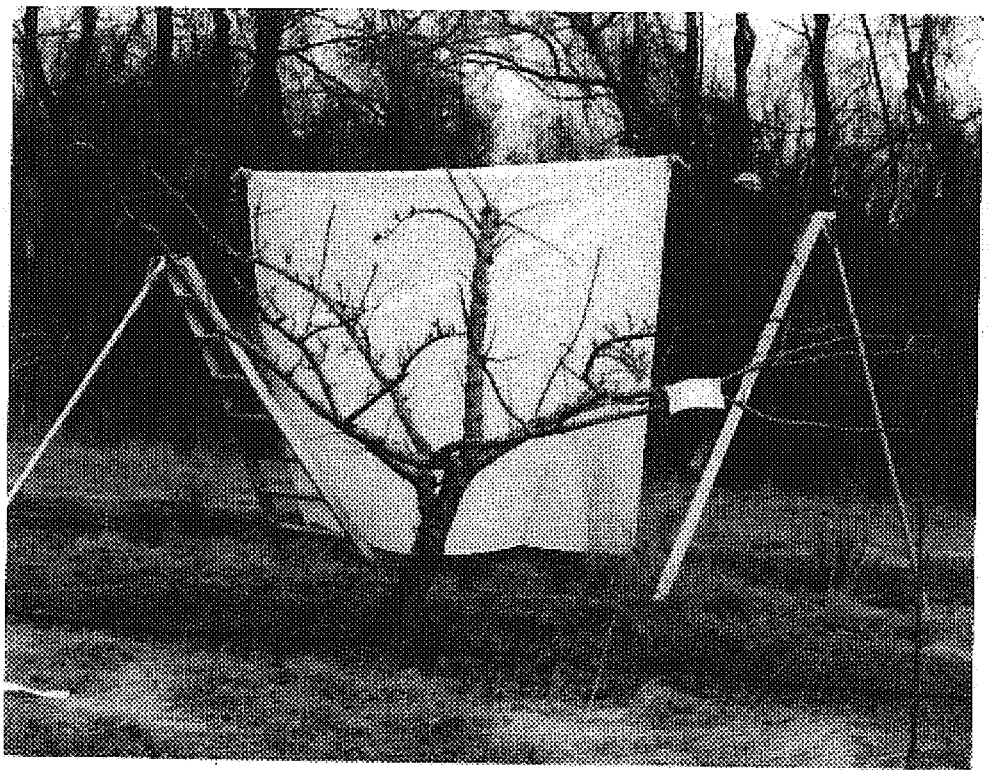
FIG. 1 illustrates the original tree growing at Coopersburg, Pa., U.S.A., while in the dormant state. The tree limbs had been artificially spread with limb spreaders and rope tie downs over the years of growth.
Figure 2:
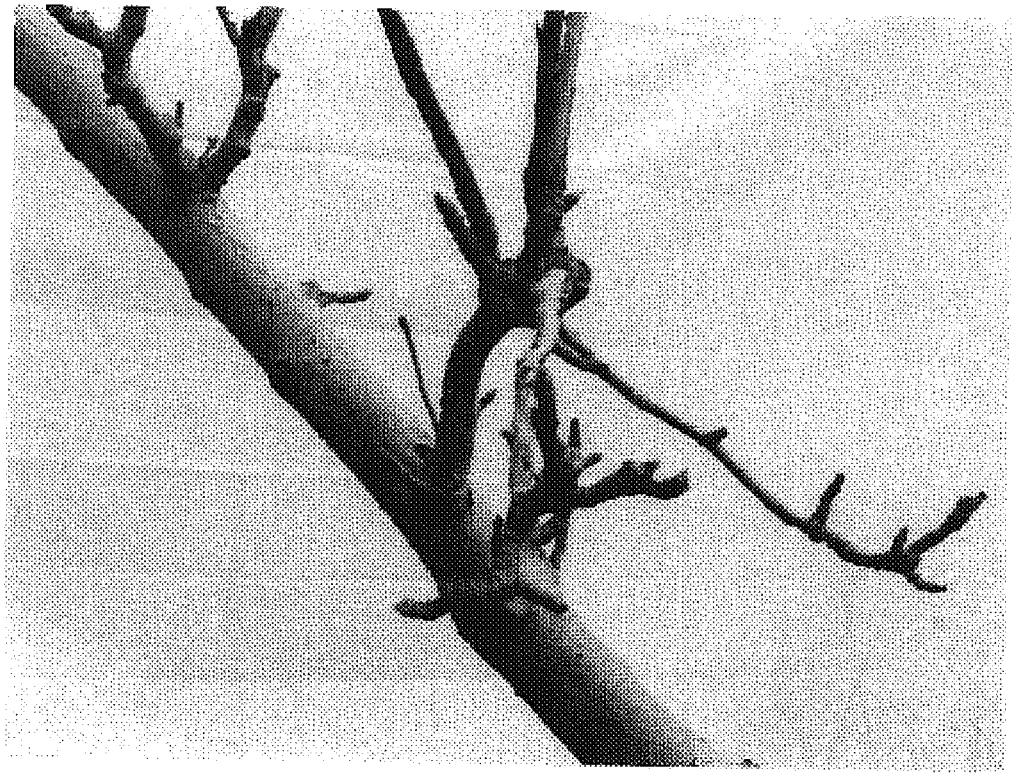
FIG. 2 illustrates a close view of a typical branch of the original tree when dormant wherein the numerous fruiting spurs are shown. Some branch scars resulting from Cicada Brood X damage during 2004 also are included and should be disregarded as being atypical.
Figure 3:
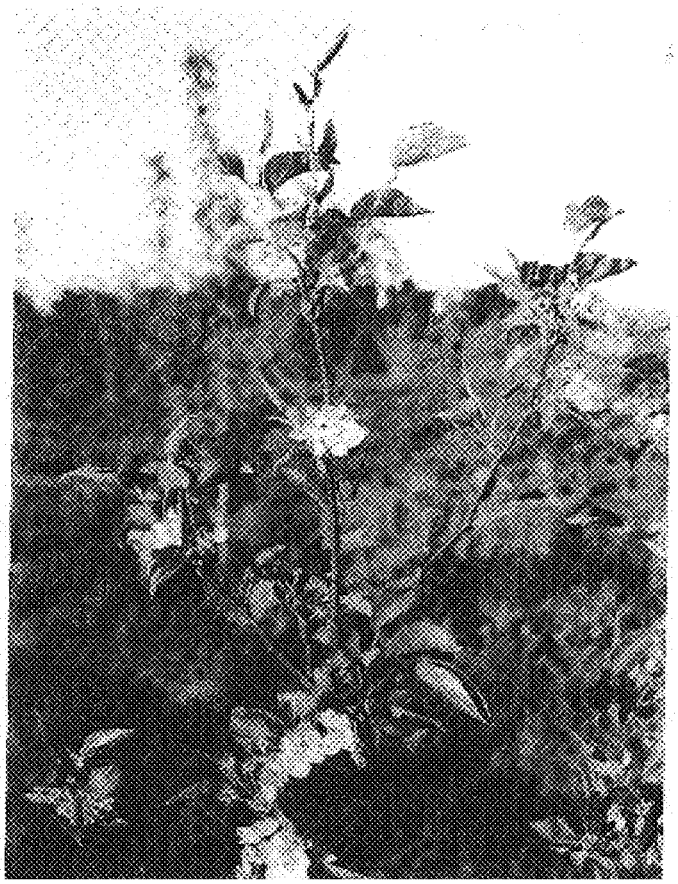

FIG. 3 illustrates a close view of a typical flowering branch of a young cloned tree of the new cultivar. The tree had been growing in the field at Germansville, Pa., U.S.A., for five years following asexual propagation by budding. Blossom clusters with and without petals are shown.

Figure 4:
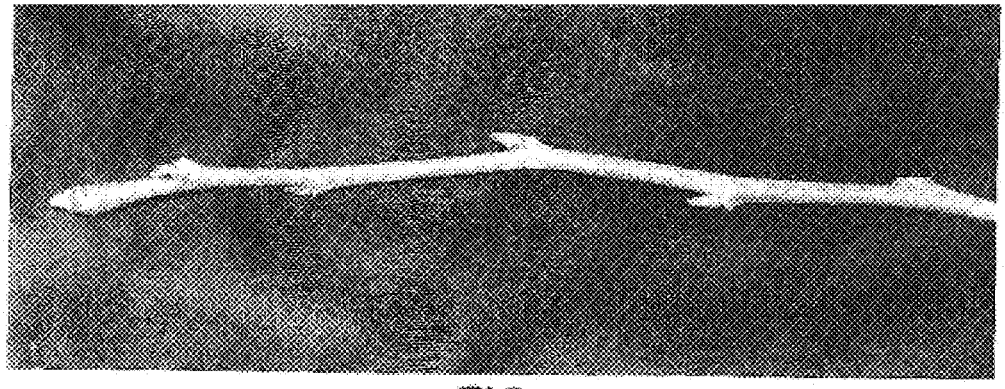
Figure 3:
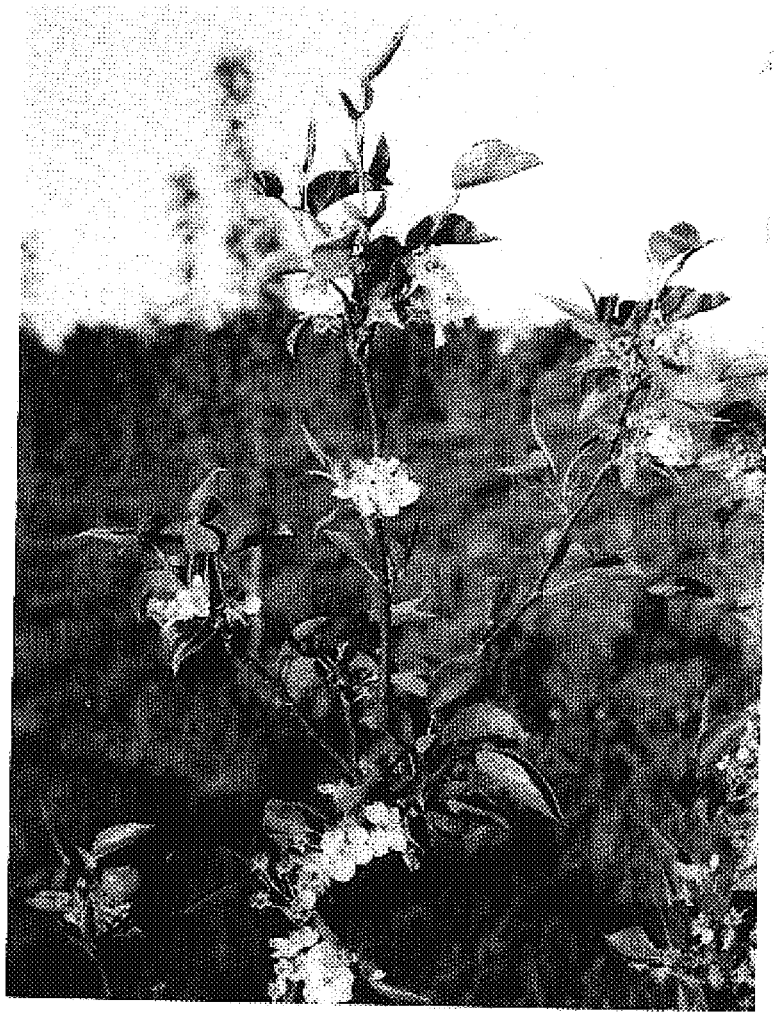
Figure 4:
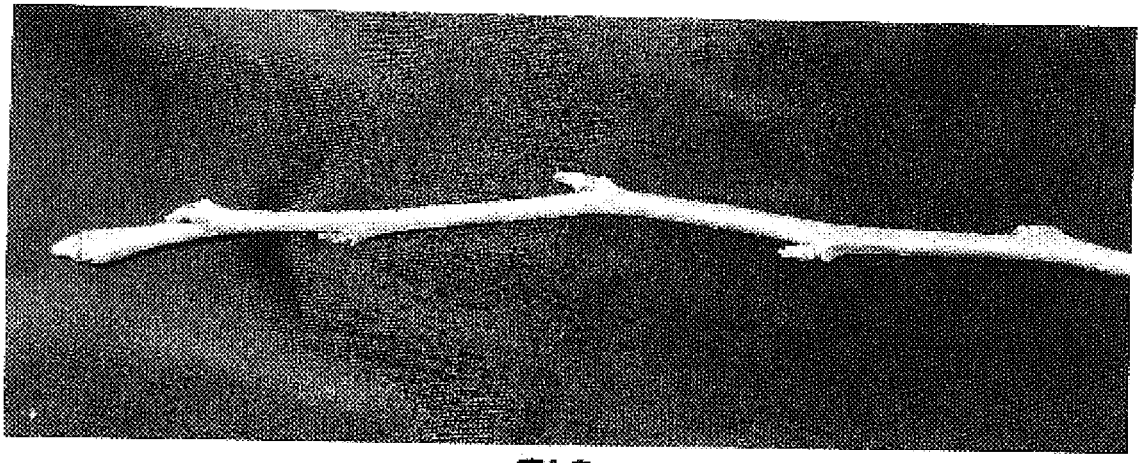

FIG. 4 illustrates a close view of a typical branch (leaves removed) of the new cultivar. The internodes, buds, and limb coloration are shown.

Figure 5:
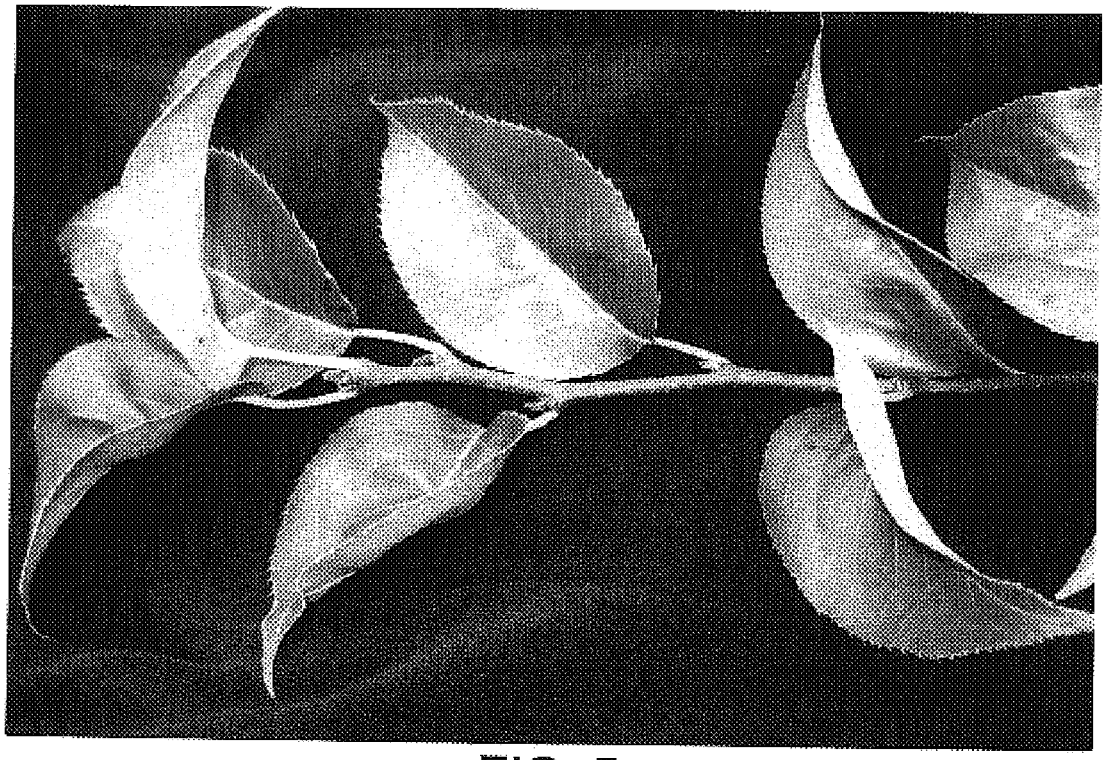

FIG. 5 illustrates a close view of a typical branch with leaves of the new cultivar.

Figure 6:
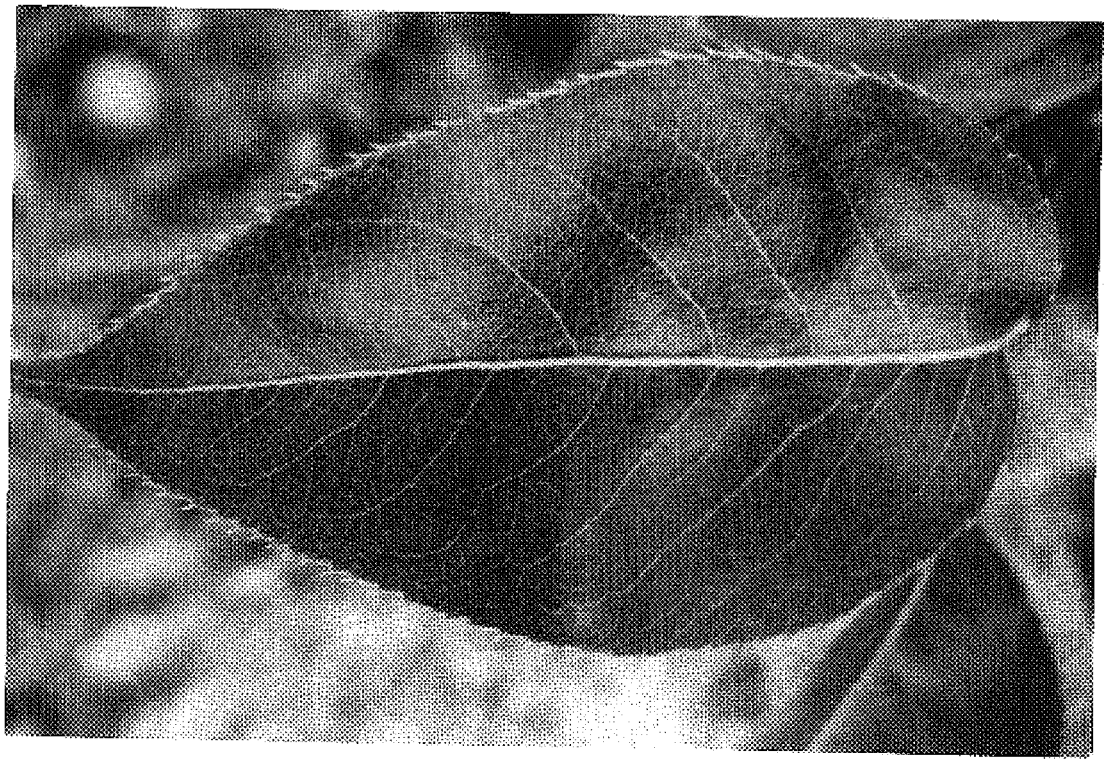

FIG. 6 illustrates a close view of a typical leaf of the new cultivar. The overall leaf shape, color, venation, margin configuration, and apex are shown.

Figure 7:
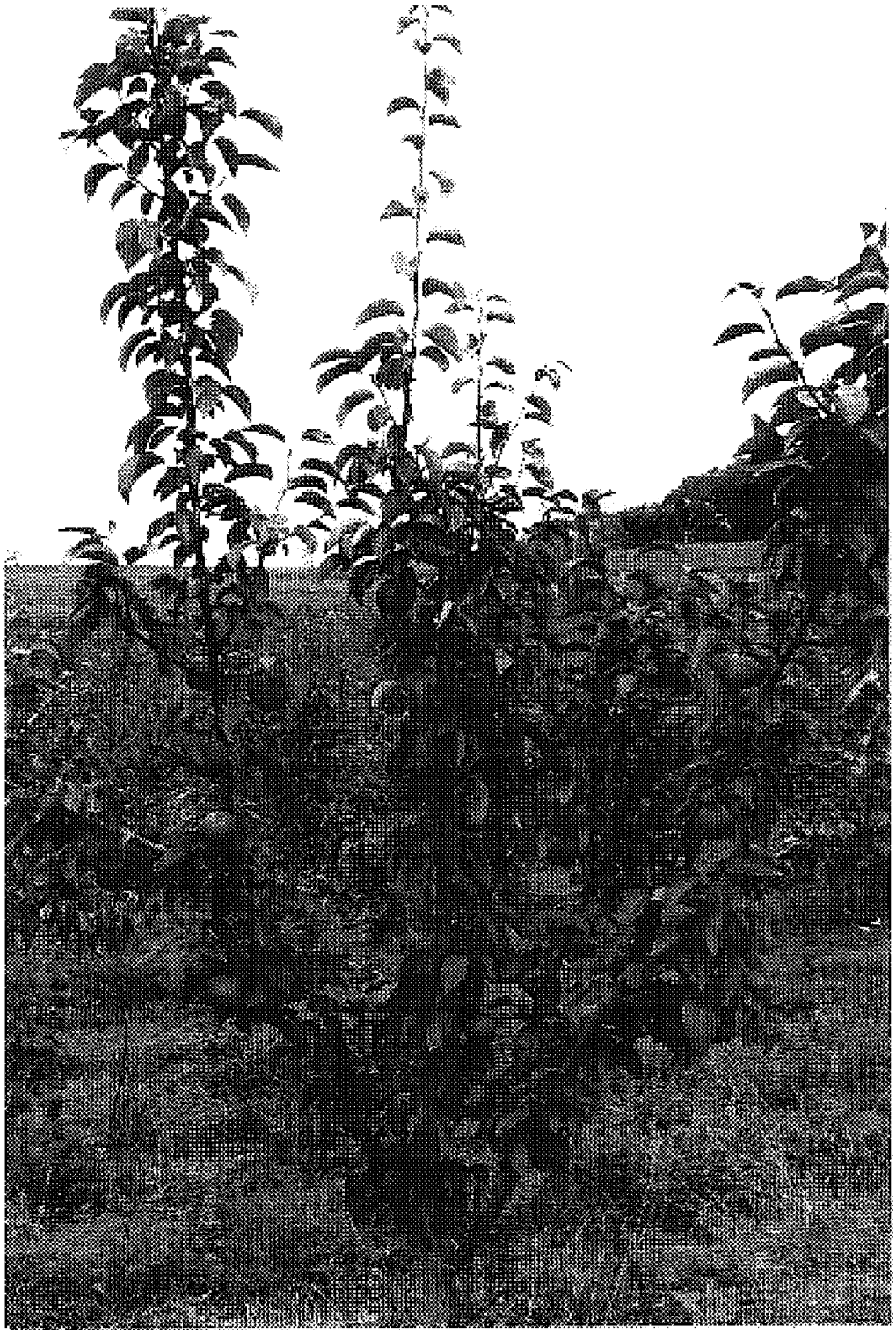

FIG. 7 illustrates the spreading growth habit of a typical tree of a young cloned tree of the new cultivar while abundantly bearing fruit. The tree had been growing in the field at Germansville, Pa., U.S.A., for five years following asexual propagation by budding. The typical well-branched upright growth habit is shown.

Figure 8:
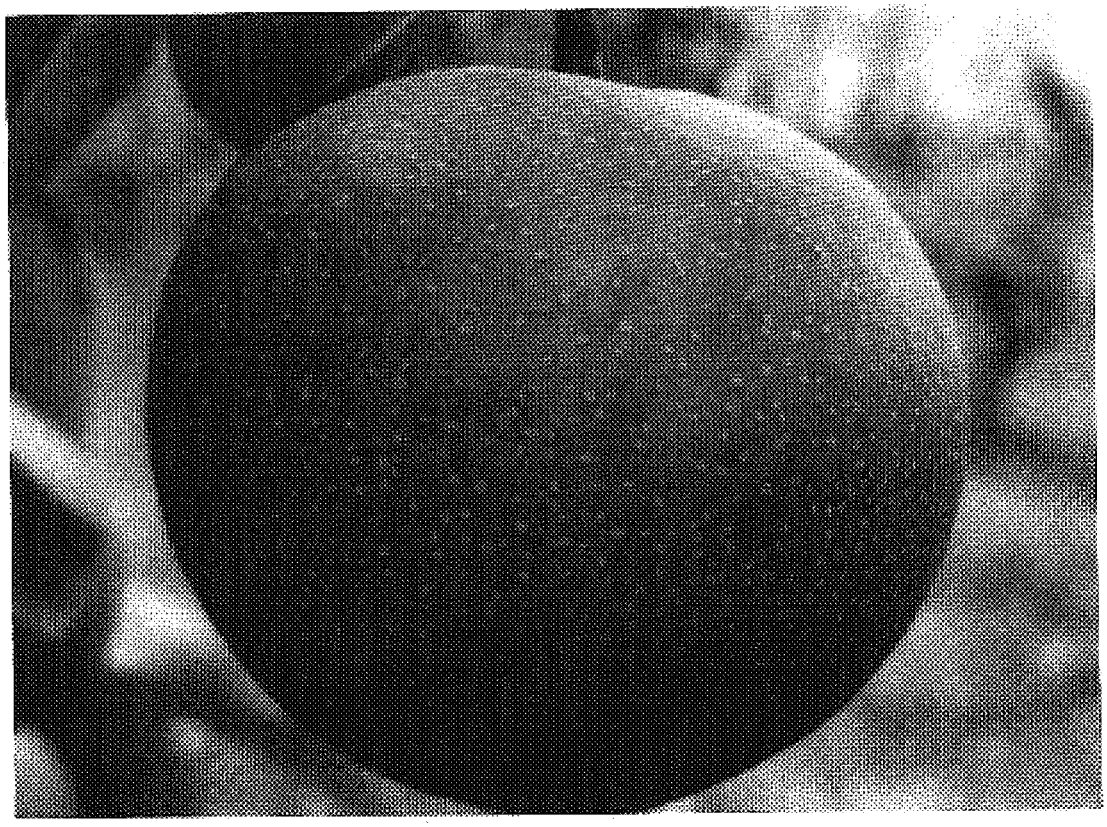

FIG. 8 illustrates a close view of a single fruit obtained from the young cloned tree of FIG. 7.

FIG. 9 illustrates the typical attractive recently harvested fruit of the new cultivar. A ruler showing dimensions in millimeters is located at the very bottom for comparative purposes.

FIG. 10 illustrates typical internal (right) and external (left) views of the fruit following approximately four months of storage. The slight darkening of the flesh shown on the internal view is attributable to the customary oxidation upon the passage of time when the flesh is exposed to air. A ruler showing dimensions in inches is included at the bottom for comparative purposes.

DETAILED DESCRIPTION

The chart used in the identification of colors described herein is The R.H.S. Colour Chart of Royal Horticultural Society, London, England. When used in some instances, ordinary color terms are to be accorded their ordinary dictionary significance. The trees described were being grown in their tenth leaf at Coopersburg, Pa., U.S.A., and at Germansville, Pa., U.S.A.

Tree:

*Origin.*—Seedling of unknown parentage.

Tree:

*Size.*—Large. The original tree has been pruned to maintain a height of approximately 14 feet. Typical heights for budded trees are approximately 5 feet following planting in the field for three years, and approximately 8 feet following planting in the field for five years.

*Growth habit.*—Moderate vigor and well-branched.

*Configuration.*—Generally upright. Limb spreaders can be utilized to further improve branch angles.

*Density.*—Somewhat open (as illustrated).

*Hardiness.*—Hardy in bud and wood.

*Fruit bearing.*—Productive. Fruit productivity commonly approaches its peak in the tenth leaf and subsequent seasons. A typical properly thinned tree in the tenth leaf commonly produces approximately 50 pears each having a weight of approximately 350 grams.

*Bearing habit.*—Generally laterally on second year or older spurs. Fruiting generally is annual except following a year when there has been an extremely heavy fruit cop. In such instance a biennial bearing habit may be displayed in the following year.

*Trunk.*—Medium in diameter, grooved, and slightly rough in texture.

Branches:

*Thickness.*—Medium.

*Size.*—Lower scaffold limbs commonly possess a diameter that is approximately ¼ to ⅓ the diameter of the trunk and their length commonly is approximately ¾ the height of the tree.

*Frequency.*—Moderate branching.

*Texture.*—Generally smooth.

*Bark color.*—Yellow-Green Group 148A.

*Lenticels.*—Commonly approximately 12 per internode on average, somewhat prominent, and tan in coloration.

Leaves:

*Size.*—Long, and approximately 11.9 cm in length on average, and approximately 6.8 cm in width on average.

*Configuration.*—Generally ovate.

*Base.*—Rounded.

*Apex.*—Acuminate.

*Margin.*—Serrulate.

*Venation.*—Pinnate with many fine branches.

*Thickness.*—Medium.

*Color.*—Upper Surface: Medium Green, near Yellow-Green Group 147A when fully mature. Under Surface: Silvery Green.

*Petiole.*—Medium in length and commonly approximately 3 cm in length on average.

Flowers:

*Season.*—Mid-season, commonly substantially concurrent with the 'Olympic' cultivar, first bud break commonly is near April 21st, and full bloom commonly is near April 30th.

*Size.*—Medium, and commonly approximately 3.5 cm in diameter on average.

*Petals.*—Five in number and obovate in configuration.

*Color.*—White, White Group 155A.

*Anthers.*—Initially purple in coloration and upon drying as the pollen dehisces assume a black coloration.

*Filaments.*—White in coloration.

*Bearing.*—Commonly in a corymb of approximately 8 to 10 flowers.

*Calyx.*—Commonly approximately 6 mm in size.

Fruit:

*Season of maturity.*—Late-season, approximately the same time as the 'Olympic' cultivar, commonly with optimum harvesting between October 8th and 15th.

*Size.*—Large, commonly 250 to 400 grams per fruit. It is recommended that the fruit be thinned in order to encourage the formation of the larger-sized fruit.

*Configuration.*—Conical to round.

*Neck.*—Absent.

*Stem.*—Medium in length, thick, and lipped.

*Cavity.*—Shallow, and acute.

*Basin.*—Obtuse.

*Calyx.*—Deciduous.

*Skin.*—Ground Color: Yellow-Green Group 153B. Surface Color: Greyed-Orange Group 167A and Greyed-Orange Group 169B. The skin bears an uneven and textured reddish-brown russet with visible tan lenticels (Yellow-Green Group 153A).

*Flesh.*—Very juicy, white (White Group 155C), crisp, and slightly coarse in texture. Equally crisp as that of the 'Olympic' cultivar but the texture is more coarse.

*Core.*—Median.

*Carpels.*—Elliptical with axial symmetry.

*Seeds.*—When fully pollinated, ten seeds develop with two seeds per carpel that are five in number. Commonly approximately 6 to 10 seeds are present per fruit. The seeds are medium-sized, commonly flattened on one side and are dark brown (Brown Group 200C) in coloration.

*Total soluble solids.*—Commonly approximately 13 to 15 Brix on average.

*Quality.*—Excellent, crisp, juicy, highly attractive with a mild flavor, and intense sweetness.

*Keeping quality.*—Possess a long storage life. Can be kept up to approximately 5 months at 32° F. without significant breakdown; however, some surface shriveling can result from prolonged storage. See FIG. 10 for satisfactory fruit appearance after approximately 4 months of storage.

What is claimed is:

1. A new and distinct Asian Pear tree that possesses the following combination of characteristics:

(a) forms attractive late-season large conical to round fruit having a mottled reddish-brown russet surface with prominent tan lenticels and a very sweet mild flavor, (b) forms a medium-sized tree having a well-branched upright growth habit, and (c) forms generally ovate medium green leaves with pinnate venation and an acuminate apex;

substantially as herein shown and described.

* * * * *